US007618392B2

(12) United States Patent
Martis et al.

(10) Patent No.: US 7,618,392 B2
(45) Date of Patent: *Nov. 17, 2009

(54) METHODS AND COMPOSITIONS FOR DETECTION OF MICROBIAL CONTAMINANTS IN PERITONEAL DIALYSIS SOLUTION

(75) Inventors: Leo Martis, Long Grove, IL (US); Mehul Patel, Sauderstown, RI (US); Joseph A. Giertych, Lake Forest, IL (US); James W. Mongoven, Long Grove, IL (US); Jacqueline A. Kunzler, Downers Grove, IL (US); William F. Owen, Jr., Durham, NC (US)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 488 days.

This patent is subject to a terminal disclaimer.

(21) Appl. No.: 11/457,330

(22) Filed: Jul. 13, 2006

(65) Prior Publication Data
US 2006/0263842 A1  Nov. 23, 2006

Related U.S. Application Data

(62) Division of application No. 10/789,320, filed on Feb. 27, 2004, now Pat. No. 7,118,857.

(51) Int. Cl.
*C12Q 1/00* (2006.01)
(52) U.S. Cl. .............. 604/29; 604/28; 435/4; 435/14; 435/29; 435/34; 436/1; 436/815; 422/1
(58) Field of Classification Search .......... None
See application file for complete search history.

(56) References Cited

U.S. PATENT DOCUMENTS

| | | | |
|---|---|---|---|
| 4,761,237 | A | 8/1988 | Alexander et al. |
| 4,886,789 | A | 12/1989 | Milner |
| 4,970,152 | A | 11/1990 | Ashida et al. |
| 5,431,496 | A | 7/1995 | Balteau et al. |
| 6,077,836 | A | 6/2000 | Milner |
| 6,248,726 | B1 | 6/2001 | Alsop et al. |
| 6,329,011 | B1 | 12/2001 | Oita |
| 6,770,148 | B1 | 8/2004 | Naggi et al. |
| 2004/0121982 | A1 | 6/2004 | Martis et al. |

OTHER PUBLICATIONS

Kanny G et al.: "Immunochemical Analysis of Peritoneal Dialysate in a Patient with Hypersensitivity to Icodextrin." Peritoneal Dialysis International: Journal of the International Society for Peritoneal Dialysis, vol. 23, Jul. 2003, pp. 405-406.
Seow Ying-Ying T et al.: "Icodextrin-associated peritonitis among CAPD patients," Nephrology Dialysis Transplantation, vol. 18, No. 9, Sep. 2003, pp. 1951-1952.
Toure Fatouma et al. "Icodextrin-induced peritonitis: Study of five cases and comparison with bacterial peritonitis," Kidney International, vol. 65, No. 2, Feb. 2004, pp. 654-660.
Povlsen J. V. et al.: "Exposure to the Peptidoglycan Contaminant in Icodextrin May Cause Sensitization of the Patient Maintained on Peritoneal Dialysis." Peritoneal Dialysis International, vol. 23, Sep. 2003, pp. 509-510.
Basile Carlo et al.: The impact of relapsing sterile icodextrin-associated pertionitis on pertioneal dialysis outcome.: Journal of Nephrology, vol. 16, May 2003, pp. 384-386.
Glorieux Griet et al.: "Specific Characteristics of Peritoneal leucocyte populations during sterile peritonitis associated with icodextrin CAPD fluids." Nephrology Dialysis Transplantation, vol. 18, No. 8, Aug. 2003, pp. 1648-1653.
Malberti F et al.: "Sterile Peritonitis Associated with the Use of Icodextrin Solutions in Patients on Peritoneal Dialysis (PD)" Nephrology Dialysis Transplantation, vol. 17, No. Abstracts Supplement 1, 2002, p. 307, XP008048088 & XXXIX Congress of the European Renal Association and the European Dialysis and Transplant Association; Copenhagen, Denmark; Jul. 14-17, 2002.
Minors S et al.:"A Sensitive Chemiluminescence Based Immunoassay For Antibody To Staphylococcal Peptidoglycan" Journal of Immunological Methods, vol. 115, No. 1, 1988, pp. 119-125.
Extraneal letter dated May 22, 2002; 2 pages.

(Continued)

*Primary Examiner*—Allison M Ford
(74) *Attorney, Agent, or Firm*—K&L Gates LLP (57) ABSTRACT

Methods and compositions for detection of microbial contaminants in peritoneal dialysis solutions are provided. The methods and compositions employ modified bioburden testing and the detection of peptidoglycan. A novel cause of aseptic peritonitis is provided—aseptic peritonitis associated with gram positive microbial contamination of a dialysis solution. Peptidoglycan is a major component of a gram positive bacterial cell wall and thus can serve as a marker for gram positive bacteria. In this regard, testing for peptidoglycans can be utilized to effectively prevent peritonitis in patients that use the peritoneal dialysis solutions, such as peritoneal dialysis solutions that contain a glucose polymer including an icodextrin and the like.

9 Claims, 5 Drawing Sheets

OTHER PUBLICATIONS

Wako Pure Chemical Industries, Ltd., Osaka, Japan, 6 pages, published prior to Feb. 27, 2004.
Vas, Stephen "Peritonitis," Peritoneal Dialysis. 3rd ed. Dordrecht, The Netherlands: Kluwer Academic Publishers, 1989:261-84.
Karanicolas et al., "Epidemic of aseptic peritonitis caused by endotoxin during chronic peritoneal dialysis," N Engl J Med 1977;296:1336-7.
Pool et al., "Differentiation between endotoxin and non-endotoxin pyrogens in human albumin solutions using an ex vivo whole blood culture assay," J Immunoassay 1999;20:79-89.
Smith et al., "Chemical peritonitis associated with intraperitoneal vancomycin," Ann Pharm 1991;25:602-3.
Charney et al., "Chemical peritonitis secondary to intraperitoneal vancomycin," Am J Kidney Dis 1991;17:76-9.
Benevent et al., "Dangers of administration of intraperitoneal amphotericin B in continuous ambulatory peritoneal dialysis," Press Med 1984;13:1844.
Tuncer et al., "Chemical peritonitis associated with high dialysate acetaldehyde concentrations," Nephrol Dial Transplant 2000;15:2037-40.
Gokal et al., "'Eosinophilic'peritonitis in continuous ambulatory peritoneal dialysis (CAPD)," Clin Nephrol 1981;15:328-330.
Wilkie et al., "Icodextrin 7.5% dialysate solution (glucose polymer) in patients with ultrafiltration failure: extension of technique survival," Perit Dial Int 1997;17:84-7.
Wolfson M., et al. "A randomized controlled trial to evaluate the efficacy and safety of icodextrin in peritoneal dialysis," Am J Kidney Dis 2002;40:1055-65.
Mujais et al., "Evaluation and management of ultrafiltration problems in peritoneal dialysis," Perit Dial Int 2000;20 (Suppl 4):S5-S21.
Pinerolo et al., "Recurrent sterile peritonitis at onset of treatment with icodextrin solution," Perit Dial Int 1999;19:491-2.
Williams, Paul, "Timely initiation of dialysis," Am J Kidney Dis 34:594-595, 1999.
Williams Paul, "Sterile/allergic peritonitis with icodextrin in CAPD patients," Perit Dial Int 2002;22:89-90.
Foggensteiner et al., "Timely initiation of dialysis—single-exchange experiences in 39 patients starting peritoneal dialysis," Perit Dial Int 2002;22:471-6.
Herring et al., "Peritoneal reaction to icodextrin in a female patient on CAPD," Perit Dial Int 2001;21:323.
Del Rosso et al., "A new form of acute adverse reaction to icodextrin in peritoneal dialysis patient," Nephrol Dial Transplant 2000;15:927-8.
Goffin et al., "Transient sterile chemical peritonitis in a CAPD patient using icodextrin," Perit Dial Int 2002;22:90-1.
Tintillier et al., "Transient sterile chemical peritonitis with icodextrin: clinical presentation, prevalence, and literature review," Perit Dial Int 2002;22:534-7.
Gokal et al., "Icodextrin-associated sterile peritonitis," Perit Dial Int 2002;22:445-8.
Dinarello et al., "Human leukocyte pyrogen test for detection of pyrogenic material in growth hormone produced by recombinant *Escherichia coli*," J Clin Microbiol 1984;20:323-9.
Poole et al., "Detection of pyrogen by cytokine release," Lancet 1988;1(8577):130.
Tsuchiya et al. "Detection of peptidoglycan and B-glucan with silkworm larvae plasma test," FEMS Immunol Medical Micrbiol 1996;15:129-34.
Ray et al. "Variability in LPS composition, antigenicity and reactogenicity of phase variants of *Bordetella pertussis*," FEMS Microbiol Lett 1991;63:211-7.
Taktak et al., "Assay of pyrogens by interleukin-6 release from monocytic cell lines," J Pharm Pharmacol 1991;43:578-82.
Fennrich et al. "Detection of endotoxins and other pyrogens using human whole blood," Dev Biol Stand 1999;101:131-9.
Matsubara et al. "*Alicyclobacillus acidiphilus* sp. Nov., a novel thermo-acidophilic, omega-alicyclic fatty acid-containing bacterium isolated from acidic beverages," Int J Syst Evol Microbiol 2002; 52:1681-5.
Royce et al., "Endotoxin-like properties of an extract from a symbiotic, eukaryotic cholerella-like green algae," J Endotoxin Res 1996;3:437-44.
Sriskandan et al., "Gram-positive sepsis," Bacterial Sepsis and Septic Shock, Philadelphia: W. B. Saunders Company, 1999:397-412.
Garner et al., "Intravenous Injection of candida-derived mannan results in elevated tumor necrosis factor alpha levels in serum," Infect Immun 1996;64:4561-6.
Schwab, John, "Phlogistic properties of peptidoglycan-polysaccharide polymers from cell walls of pathogenic and normal flora bacteria which colonize humans," Infect Immun 1993;61:4535-9.
Henderson et al., "Bacterial modulins: a novel class of virulence factors which cause host tissue pathology by inducing cytokine synthesis," Microbiol Rev 1996;60:316-41.
Nakagawa et al. "Evaluation of the in vitro pyrogen test system based on proinflammatory cytokine release from human monocytes: Comparison with a human whole blood culture test system and with the rabbit pyrogen test," Clin Diag Lab Immunol 2002;9:588-97.
Burke et al., "Direct determination of polyglucose metabolites in plasma using anion-exchange chromatography with pulsed amperometric detection," J Chromatogr B 1997;693:353-7.
Weary et al., "Validating an LAL chromogenic substrate pyrogen test for large volume parenterals," Detection of bacterial endotoxin with limulus amebocyte lysate test, New York: Alan R. Liss, 1987:307-22.
European Pharmacopoeia, Pyrogens, 4th ed. Strasbourg, France: Council of Europe, 2002:131-2.
Kobayashi et al, "Detection of peptidoglycan in human plasma using the silkworm larvae plasma test," FEMS Immunology and Medical Microbiology, 28, (2000) 49-53.
Inada et al., "A silkworm larvae plasma test for detecting peptidoglycan in cerebrospinal fluid is useful for the diagnosis of bacterial meningitis," Microbiol. Immunol., 47(10), 701-707, 2003.
Tsuchida et al., "Detection of peptidoglycan and endotoxin in dialysate, using silkworm larvae plasma and limulus amebocyte lysate methods," Nephron 1997, 75, 438-443.
Hiyoshi et al, "Silkworm Larvae Plasma" (Source Unknown), 1999, 73, p. 1222-1226.
"The Prokaryotic Cell: Bacteria;" http://www/cat/cc.md.us/courses/bio141/lecguide/unit1/prostruct/cw.html accessed Apr. 27, 2005.
Mangram et al., "Outbreak of sterile peritonitis among continuous cycling peritoneal dialysis patients," Kidney Int. 1998, vol. 54, pp. 1367-1371.
Goffin et al., Nephrol Dial Transplant, Nov. 2003, vol. 18, pp. 2482-2485.
Martin et al., Advances in Peritoneal Dialysis, Sep. 4, 2003, vol. 19, pp. 191-194.

METHODS AND COMPOSITIONS FOR DETECTION OF MICROBIAL CONTAMINANTS IN PERITONEAL DIALYSIS SOLUTION

CROSS REFERENCE TO RELATED APPLICATIONS

The present application is a divisional of U.S. application Ser. No. 10/789,320 filed on Feb. 27, 2004, the disclosure of which is herein incorporated by reference.

BACKGROUND

The present invention generally relates to the detection of gram positive microbial contaminants. More specifically, the present invention relates to methods and compositions that employ modified bioburden testing and the detection of peptidoglycan in peritoneal dialysis solutions. Peptidoglycans are major cell wall components of gram positive organisms and thus serve as a good marker of these microbes.

Due to disease or insult or other causes, the renal system can fail. In renal failure of any cause, there are several physiological derangements. The balance of water, minerals (e.g., Na, K, Cl, Ca, P, Mg, $SO_4$) and the excretion of a daily metabolic load of fixed ions is no longer possible in renal failure. During renal failure, toxic end products of nitrogen metabolism (e.g., urea, creatinine, uric acid, and the like) can accumulate in blood and tissues.

Dialysis processes have been devised for the separation of elements in a solution by diffusion across a semi-permeable membrane (diffusive solute transport) across a concentration gradient. Examples of dialysis processes include hemodialysis, peritoneal dialysis and hemofiltration.

Hemodialysis treatment utilizes the patient's blood to remove waste, toxins, and excess water from the patient. The patient is connected to a hemodialysis machine and the patient's blood is pumped through the machine. Catheters or the like are inserted into the patient's veins and arteries to connect the blood flow to and from the hemodialysis machine. Waste, toxins, and excess water are removed from the patients blood and the blood is infused back into the patient. Hemodialysis treatments can last several hours and are generally performed in a treatment center about three or four times per week.

To overcome the disadvantages often associated with classical hemodialysis, other techniques were developed, such as peritoneal dialysis. Peritoneal dialysis utilizes the patient's own peritoneum as a semipermeable membrane. The peritoneum is the membranous lining of the body cavity that, due to the large number of blood vessels and capillaries, is capable of acting as a natural semipermeable membrane.

In peritoneal dialysis, a sterile dialysis solution is introduced into the peritoneal cavity utilizing a catheter or the like. After a sufficient period of time, an exchange of solutes between the dialysate and the blood is achieved. Fluid removal is achieved by providing a suitable osmotic gradient from the blood to the dialysate to permit water outflow from the blood. This allows a proper acid-base, electrolyte and fluid balance to be returned to the blood. The dialysis solution is simply drained from the body cavity through the catheter. Examples of different types of peritoneal dialysis include continuous ambulatory peritoneal dialysis, automated peritoneal dialysis and continuous flow peritoneal dialysis.

Standard peritoneal dialysis solutions contain dextrose to effect transport of water and metabolic waste products across the peritoneum. Although dextrose has the advantage of being relatively safe and inexpensive, it has a number of disadvantages. Because of the small size, dextrose is rapidly transported through the peritoneum, thus leading to the loss of osmotic gradient and loss of ultrafiltration within about 2 to 4 hours of infusion. It has been suggested that the ultrafiltration characteristics of peritoneal dialysis solutions could be improved by replacing dextrose with large molecular weight substances, such as glucose polymers. An example of a novel high molecular weight agent is icodextrin. Dialysis solutions containing icodextrin are commercially available and have been found to be useful in treating patients with end stage renal disease.

Peritonitis is a major complication of peritoneal dialysis. Clinical suspicion of peritonitis is prompted by the development of a cloudy-appearing dialysate in combination with variable clinical manifestations that may include abdominal pain, nausea, vomiting, diarrhea and fever. See, for example, Vas S I: Peritonitis. In: Nolph K D, ed. *Peritoneal Dialysis*. $3^d$ ed. Dordrecht, The Netherlands: Kluwer Academic Publishers, 1989:261-84. Most episodes of peritonitis are caused by intraperitoneal bacterial infections, and the diagnosis is usually readily established by positive dialysate cultures. However, there are several well documented causes of non-infectious or sterile peritonitis. Aseptic or sterile peritonitis, which also is described as aseptic, chemical, or culture-negative peritonitis, is typically caused by a chemical or a foreign body irritant.

One of the major outbreaks of sterile peritonitis among patients on peritoneal dialysis occurred in 1977. This was attributed to intrinsic and occult endotoxin contamination of dialysis solution. Suspected provocative batches of peritoneal dialysate had endotoxin levels in the range of 2 to 2.5 endotoxin units (EU)/mL. See, for example, Karanicolas S, Oreopoulos D G, Izatt S H, et al: Epidemic of aseptic peritonitis caused by endotoxin during chronic peritoneal dialysis, *N Engl J Med* 1977; 296:1336-7. A similar epidemic of aseptic peritonitis caused by endotoxin contamination in continuous cycling peritoneal dialysis patients was reported in 1998. See, for example, Mangram A J, Archbald L K, Hupert M, et al: Outbreak of sterile peritonitis among continuous cycling peritoneal dialysis patients, *Kidney Int* 1988; 54:1367-71. Other reported causes of aseptic peritonitis include intraperitoneal administered vancomycin (See, for example, Smith T, Baile G, Eisele G: Chemical peritonitis associated with intraperitoneal vancomycin, *Ann Pharm* 1991; 25:602-3, and Chancy D I, Gouse S F: Chemical peritonitis secondary to intraperitoneal vancomycin, *Am J Kidney Dis* 1991; 17:76-9), amphotericin B (See, for example, Benevent D, El Akoun N, Lagarde C: Dangers of administration of intraperitoneal amphotericin B in continuous ambulatory peritoneal dialysis, *Press Med* 1984; 13:1844), and acetaldehyde (See, for example, Tuncer M, Sarikaya M, Sezer T, et al: Chemical peritonitis associated with high dialysate acetaldehyde concentrations, *Nephrol Dial Transplant* 2000; 15:2037-40). A unique form of aseptic peritonitis, eosinophilic peritonitis, is a much more common entity that can occur shortly after the start of peritoneal dialysis. See, for example, Gokal R, Ramos J M, Ward M K, et al: 'Eosinophilic peritonitis' in CAPD, *Clin Nephrol* 1981; 15:328-330.

As previously discussed, glucose polymers, such as icodextrin, can be used in place of dextrose in peritoneal dialysis solutions. Icodextrin is a polymer of glucose derived from the hydrolysis of corn starch. It has a molecular weight of 12-20, 000 Daltons. Peritoneal dialysis solutions containing icodextrin as the osmotic agent are, in general, used for long dwell (>4 hour) exchanges. The majority of glucose molecules in icodextrin are linearly linked with a (1-4) glucosidic bonds (>90%) while a small fraction (<10%) is linked by a (1-6) bonds.

Icodextrin was introduced into clinical practice in the United Kingdom in 1994 and in other European countries beginning in 1996. The clinical advantages of icodextrin for long dwells, especially in patients with high and high average transport status and loss of ultrafiltration, is well-accepted and contributed to its global popularity. See, for example, Wilkie M E, Plant M J, Edwards L, et al: Icodextrin 7.5% dialysate solution (glucose polymer) in patients with ultrafiltration failure: extension of technique survival, *Perit Dial Int* 1997; 17:84-7; Wolfson M, Piraino B, Hamburger R J, Morton A R, for the Icodextrin Study Group: A randomized controlled trial to evaluate the efficacy and safety of icodextrin in peritoneal dialysis, *Am J Kidney Dis* 2002; 40:1055-65; and Mujais S, Nolph K, Gokal R, et al: Evaluation and management of ultrafiltration problems in peritoneal dialysis, *Perit Dial Int* 2000; 20(Suppl 4):S5-S21.

Since the introduction of icodextrin for use in peritoneal dialysis solutions, sporadic cases of aseptic peritonitis have been reported. See, for example, Pinerolo M C, Porri M T, D'Amico G: Recurrent sterile peritonitis at onset of treatment with icodextrin, *Perit Dial Int* 1999; 19:491-2; Williams P F: Timely initiation of dialysis. *Am J Kidney Dis* 34:594-595, 1999; Williams P F, Foggensteiner L: Sterile/allergic peritonitis with icodextrin in CAPD patients, *Perit Dial Int* 2002; 22:89-90; Foggensteiner L, Bayliss J, Moss H, et al: Timely initiation of dialysis—single-exchange experiences in 39 patients starting peritoneal dialysis, *Perit Dial Int* 2002; 22:471-6; Heering P, Brause M, Plum J, et al: Peritoneal reaction to icodextrin in a female patient on CAPD. *Perit Dial Int* 2001; 21:321-2; Del Rosso G, Di Liberato L, Pirilli A, et al: A new form of acute adverse reaction to icodextrin in peritoneal dialysis patient, *Nephrol Dial Transplant* 2000; 15:927-8; Goffin E, Scheiff J M: Transient sterile chemical peritonitis in a CAPD patient using icodextrin, *Perit Dial Int* 2002; 22:90-1; Tintillier M, Pochet J M, Christophe J L, Scheiff J M, et al: Transient sterile chemical peritonitis with icodextrin: clinical presentation, prevalence, and literature review, *Perit Dial Int* 2002; 22:534-7; and Gokal R: Icodextrin-associated sterile peritonitis, *Perit Dial Int* 2002; 22:445-8. These patients typically presented with cloudy dialysate, no abdominal pain, and dialysate cell counts varying from 300 to 3500/mm$^3$, with variable percentages of neutrophils, lymphocytes, and macrophages. In general, there is no change in ultrafiltration profile or peritoneal permeability for solutes. Cultures were invariably negative with no evidence of peritoneal or peripheral blood eosinophilia. Moreover, all solution components and endotoxin levels fell within the product specifications, and the icodextrin-based peritoneal dialysis solutions met all current Pharmacopoeia standards. Prompted by these reports, in 2001, the manufacturer of the icodextrin-containing solution (BAXTER HEALTHCARE CORPORATION) modified the Summary of Product Characteristics (SPC) to include cloudy effluent as an "undesirable side effect" of icodextrin. Relying on information from a global pharmacovigilence program, a greater than 10× increase in the reported cases of aseptic peritonitis associated with icodextrin was noted in 2002. A voluntary worldwide recall of several hundred batches of newly manufactured and/or released icodextrin-containing dialysis solution was prompted.

Parenteral pharmaceutical products are required to be free of contaminating substances, such as substances that can cause fever. Because endotoxins derived from gram-negative bacteria are the most common contaminant in parenteral products, the historic pyrogens of concern are LPS. Current Pharmacopeia standards are that one of two tests for pyrogenic contamination is applied to parenteral products. These tests are the rabbit pyrogen test and the LAL assay. Although generally reliable, both tests have shortcomings. The rabbit test relies on a febrile response that in turn depends upon the elaboration of pyrogenic cytokines. The rabbit pyrogen testing may be falsely negative, if the pyrogen is at a concentration too low to induce a systemic response, but of sufficient magnitude to produce a local inflammatory reaction. In turn, the more sensitive LAL test does not detect pyrogens other than LPS. Pyrogens, like viruses, fungi, DNA, gram-positive exotoxins, or bacterial cell wall components from gram positive bacteria, such as peptidoglycan and the like, will not be detected by the LAL test. See, for example, Dinarello C A, O'Conner J V, LoPreste G: Human leukocyte pyrogen test for detection of pyrogenic material in growth hormone produced by recombinant *Escherichia coli, J Clin Microbiol* 1984; 20:323-9; Poole S, Thorpe R, Meager A, et al: Detection of pyrogen by cytokine release, *Lancet* 1988; 1(8577):130; Ray A, Redhead K, Selkirk S, et al: Variability in LPS composition, antigenicity and reactogenicity of phase variants of *Bordetella pertussis, FEMS Microbiol Lett* 1991; 63:211-7; Taktak Y S, Selkirk S, Bristow A F, et al: Assay of pyrogens by interleukin-6 release from monocytic cell lines, *J Pharm Pharmacol* 1991; 43:578-82; and Fennrich S, Fischer M, Hartung T, et al: Detection of endotoxins and other pyrogens using human whole blood, *Dev Biol Stand* 1999; 101:131-9.

The global outbreak of aseptic peritonitis observed with icodextrin-based peritoneal dialysis solutions as discussed above serves as a sentinel example of how contemporary parenteral products with microbial, non-endotoxin contaminants may be considered safe under Pharmacopoeia standards but provoke adverse clinical effects. Therefore, a need exists to provide improved standards for parenteral products that employ detection procedures to better ensure that the parenteral products are effectively free of contaminating substances.

SUMMARY

The present invention generally relates to the detection of gram positive microbial contaminants. In particular, the present invention relates to methods and compositions that employ modified bioburden testing and the detection of peptidoglycan in peritoneal dialysis solutions, raw materials that can be used to make the peritoneal dialysis solutions and/or at any suitable stage in the manufacturing of same. The inventors have surprisingly discovered a novel cause of aseptic peritonitis—aseptic peritonitis associated with gram positive microbial contamination of a dialysis solution. Peptidoglycan is a major component of a gram positive bacterial cell wall and thus can serve as a marker for gram positive bacteria. Thus, testing for peptidoglycans can be utilized to effectively prevent peritonitis in patients that use the peritoneal dialysis solutions, such as peritoneal dialysis solutions that contain a glucose polymer including an icodextrin and the like.

Icodextrin is derived from corn starch, a natural product. It is well known that products of natural origin are contaminated with a wide variety of micro-organisms. The inventors have found that some natural products, such as corn starch, contain an acidophilic thermophilic bacteria, such as *Alicyclobacillus acidocaldariuos*. The later organism is ubiquitous in the food industry, particularly in acidic beverages. It is the alicyclobacillus that produces guaiacol, which is a causative substance for an off flavour orange juice. See, for example, Matsubara H, Goto K, Matsumara T, et al. Alicyclobacillus acidiphilus sp. Nov., a novel thermo-acidophilic, omega-alicyclic fatty acid-containing bacterium isolated from acidic beverages. Int J Syst Evol Microbiol 2002; 52:1681-5.

Peritoneal dialysis solutions and parenteral solutions in general have not been recognized to have been contaminated by this organism or its degradation products. This is mainly because the current testing procedure for microbial contamination of peritoneal dialysis solutions and parenteral solutions in general are not capable of detecting this organism or its degradation products.

In an embodiment, the present invention provides a method for manufacturing a peritoneal dialysis solution. The method includes providing a glucose polymer. In one embodiment, the method includes conducting a modified bioburden testing as described in various Pharmacopeias but under new conditions to detect the presence of certain gram positive organisms. Specifically, the method includes bioburden testing for gram positive organisms, such as acidophilic thermophilic organisms, at about a pH of about 4.0 to about 5.0 and a temperature of about 50° C. to about 60° C. in addition to at a pH of about 7.0 to about 7.4 and at room temperature as described in various Pharmacopeias. If the bioburden meets Pharmacopoeia standards, the glucose polymer can then be safely used to make the peritoneal dialysis solution.

In another embodiment, the method for manufacturing a peritoneal dialysis solution includes providing a glucose polymer. The method also includes adding a reagent to the glucose polymer wherein the reagent is capable of reacting with a peptidoglycan and determining an amount of the peptidoglycan using the reagent. If it is determined that a sufficiently low level of the peptidoglycan is present, the glucose polymer is then used to make the peritoneal dialysis solution.

In an embodiment, the reaction with the reagent initiates a serine protease cascade.

In an embodiment, the serine protease cascade includes a prophenol oxidase cascade.

In an embodiment, the reagent is derived from a silkworm larvae plasma.

In an embodiment, the amount of peptidoglycan is further determined by a calorimetric measurement in response to the reaction between the peptidoglycan and the reagent.

In an embodiment, the sufficiently low level of the peptidoglycan is about 10 ng/mL or less.

In an embodiment, the glucose polymer includes an icodextrin.

In an embodiment, the reagent is added to the peritoneal dialysis solution including a glucose polymer.

In an embodiment, the present invention provides removing the peptidoglycan to provide the sufficiently low level of same if it is determined that the sufficiently low level of the peptidoglycan is not present.

In another embodiment, the present invention provides a method of providing peritoneal dialysis to a patient. The method includes preparing a peritoneal dialysis solution utilizing a reagent to ensure that the peritoneal dialysis solution has a sufficiently low level of a peptidoglycan so as to prevent peritonitis in the patient; and providing the peritoneal dialysis solution to the patient.

In an embodiment, the peritoneal dialysis solution includes a glucose polymer-based solution, such as a glucose polymer-based solution that includes an icodextrin and/or the like.

In an embodiment, the peritoneal dialysis includes an automated peritoneal dialysis, a continuous ambulatory peritoneal dialysis and the like.

In an embodiment, the patient is monitored for peritonitis during peritoneal dialysis. For example, a dialysis effluent can be collected from the patient to determine an IL-6 response that correlates to an incidence of peritonitis.

In an embodiment, the reagent is used to determine if the amount of the peptidoglycan exceeds about 10 ng/mL in the peritoneal dialysis solution prior to use during peritoneal dialysis.

In yet another embodiment, the present invention provides a method of testing a peritoneal dialysis solution for a presence of a gram positive organism that exceeds a level sufficient to cause peritonitis. The method includes adding a reagent to the peritoneal dialysis solution wherein the reagent is capable of reacting with peptidoglycan to initiate a serine protease cascade; and determining the amount of the peptidoglycan. For example, the glucose polymer-based solution can be tested to determine if the amount of peptidoglycan exceeds about 10 ng/mL.

In still yet another embodiment, the present invention provides a glucose polymer composition that includes a reagent capable of reacting with a peptidoglycan. In an embodiment, a level of peptidoglycan can be established above which the product would produce sterile peritonitis.

In an embodiment, use of affinity columns with resins that bind peptidoglycan can be used to minimize the contamination of peptidoglycan in glucose polymers.

An advantage of the present invention is to provide improved peritoneal dialysis solutions.

Another advantage of the present invention is to provide improved methods for manufacturing and using peritoneal dialysis solutions that employ a detection protocol to determine the presence of peptidoglycan in the peritoneal dialysis solution.

Yet another advantage of the present invention is to provide improved testing procedures that can be employed to prevent peritonitis in patients that receive peritoneal dialysis therapy.

Yet still another advantage of the present invention is to provide an improved icodextrin composition that utilizes a detection procedure in the manufacture thereof to determine the presence of peptidoglycan.

Additional features and advantages of the present invention are described in, and will be apparent from, the following Detailed Description of the Invention and the figures.

DETAILED DESCRIPTION

The present invention generally relates to the detection of gram positive organisms and fragments thereof. In particular, the present invention relates to methods and compositions that employ a modified bioburden test and the detection of peptidoglycan in peritoneal dialysis solutions. The inventors have surprisingly discovered a novel cause of aseptic peritonitis—aseptic peritonitis associated with gram positive microbial contamination of a dialysis solution. Peptidoglycan is a major component of a gram positive bacterial cell wall and thus can serve as a marker for gram positive bacteria. In this regard, testing for peptidoglycans can be utilized to effectively prevent peritonitis in patients that use the peritoneal dialysis solutions, such as peritoneal dialysis solutions that contain a glucose polymer including an icodextrin and the like.

Aseptic peritonitis associated with icodextrin-based peritoneal dialysis solutions is believed to be the largest adverse event reported for a peritoneal dialysis solution due to a contaminant of microbial origin. Based on the experimental investigations as described in detail below, this suggests that peptidoglycan in the icodextrin-based peritoneal dialysis solution was the causative agent of aseptic peritonitis. Further, pharmacovigilence data as detailed below supports the effectiveness of the corrective action and manufacturing screening procedure to prevent the occurrence of peritonitis. These findings illustrate that while endotoxin is deservedly one of the more worrisome bacterial product that can cause adverse effects to patients, it is not the sole one. In this regard, non-endotoxin pyrogens, such as peptidoglycans, that have not been previously identified, are capable of producing clinically significant inflammation. Thus, this demonstrates that parenteral pharmaceutical products that pass the compendial tests and so meet Pharmacopoeia standards may still require a further level of testing to effectively determine the efficacy and safe use of such products to better ensure quality of life issues associated with use of same.

In the present invention, non-LPS pyrogen contamination was recognized as a problem because peritoneal dialysis exchanges permitted the direct observation of peptidoglycan-induced inflammation in situ. Peptidoglycan is a heteropolymer formed from (1-4) linked N-acetylmuramic acid and N-acetyl-D-glucosamine residues crosslinked by peptide bridges. See, for example, Royce C L, Pardy R L: Endotoxin-like properties of an extract from a symbiotic, eukaryotic cholerella-like green algae, J Endotoxin Res 1996; 3:437-44. The glycan backbone is chemically homogenous, whereas the peptides cross-linking the sugars vary. Peptidoglycan occupies approximately 40% by weight of gram positive cell wall, but about 1-10% of the total weight of the gram negative cell walls. Royce C L, Pardy R L: Endotoxin-like properties of an extract from a symbiotic, eukaryotic cholerella-like green algae, J Endotoxin Res 1996; 3:437-44. Peptidoglycan and another cell wall constituent, lipoteichoic acid, include virtually all of the major inflammatory inducing components of gram-positive cellular walls. See, for example, Sriskandan S, Cohen J: Gram-positive sepsis, In: Opal S M, Cross A S, eds. Bacterial Sepsis and Septic Shock, Philadelphia: W. B. Saunders Company, 1999:397-412.

Like endotoxins, peptidoglycans can induce cytokine production in a wide variety of cells and have long been recognized to have immunomodulatory actions. See, for example, Gamer R E, Hudson J A: Intravenous injection of candida-derived mannan results in elevated tumor necrosis factor alpha levels in serum, Infect Immun 1996; 64:4561-6; and Schwab J: Phlogistic properties of peptidoglycan-polysaccharide polymers from cell walls of pathogenic and normal flora bacteria which colonize humans, Infect Immun 1993; 61:4535-9. However, peptidoglycans are several orders of magnitude less potent than endotoxins as provocateurs of these biological effects. See, for example, Henderson B, Poole S, Wilson M: Bacterial modulins: a novel class of virulence factors which cause host tissue pathology by inducing cytokine synthesis, Microbiol Rev 1996; 60:316-41; and Nakagawa Y, Maeda H, Murai T: Evaluation of the in vitro pyrogen test system based on proinflammatory cytokine release from human monocytes: Comparison with a human whole blood culture test system and with the rabbit pyrogen test, Clin Diag Lab Immunol 2002; 9:588-97. For example, the minimum pyrogenic dose of peptidoglycans in rabbits is 7.3 µg/kg, while that of endotoxins is 0.0027 µg/kg. See, for example, Henderson B, Poole S, Wilson M: Bacterial modulins: a novel class of virulence factors which cause host tissue pathology by inducing cytokine synthesis, Microbiol Rev 1996;60:316-41.

In addition to the absence of pyrogenic containing substances, safety of parenteral products are generally defined by Pharmacopoeia tests to determine their sterility. Bacterial cultures are generally performed at neutral pH using an incubation temperature between 20-35° C. These are suboptimal conditions for the growth of thermophilic, acidophilic microorganisms such as Alicyclobacillus acidocaldarius that require an acid medium and elevated temperature for growth. Therefore, routinely employed "sterility definitions" and the supporting assays may fail to detect microorganisms that do not grow under conventional conditions. In an embodiment of the present application, acid hydrolysis at an elevated temperature is used for hydrolysis of starch to produce icodextrin. These manufacturing conditions are suitable for the growth of Alicycclobacillus acidocadarius, but discordant with those used to determine sterility based on bioburden.

As referenced above, a detailed description of the investigative findings are provided below in accordance with an embodiment of the present invention by way of example and without limitation:

Chemical and Physical Investigations

The majority of glucose molecules in icodextrin are linearly linked with a (1-4) glucosidic bonds (>90%), while a small fraction (<10%) are linked by a (1-6) bonds. Molecular weight distribution of icodextrin was performed by gel permeation chromatography. The distribution of a(1-*6) and a(l-*4) glucosidic links in icodextrin was assessed by nuclear magnetic resonance spectroscopy. Volatile and semi-volatile organic impurities were examined by high performance liquid chromatography and mass spectroscopy.

Dialysate Effluent Analysis

Dialysate effluent samples from patients were analyzed for icodextrin metabolites, triglycerides, total protein and selective pyrogenic cytokines (IL-6, IL-1 and TNF-a). Icodextrin metabolites were assayed using high performance anion exchange chromatography with pulsed amperometric detection. See, for example, Burke R A, Hvizd M G, Shockley T R: Direct determination of polyglucose metabolites in plasma using anion-exchange chromatography with pulsed amperometric detection, J Chromatogr B 1997; 693:353-7. Triglyceride and protein analysis were performed with Boehringer Mannheim/Hitachi 911 Chemistry analyzer. Cytokine measurements were made using ELISA kits (R&D Systems, Minneapolis, Minn.).

Measurement of Pyrogens

Endotoxin concentration in icodextrin solution was determined by a fixed point chromogenic LAL test. See, for example, Weary M, Dubczak J, Wiggins J, et al: Validating an LAL chromogenic substrate pyrogen test for large volume parenterals, In: Watson S W, Levin J, Novitsky T J, eds, Detection of bacterial endotoxin with limulus amebocyte lysate test. New York: Alan R. Liss, 1987:307-22. Rabbit pyrogen test was performed in accordance with the guidelines provided in the European Pharmacopeia. European Pharmacopoeia, Pyrogens, 4$^{th}$ ed. Strasbourg, France: Council of Europe, 2002:131-2. An ex vivo pyrogen test that measures IL-6 response in freshly isolated peripheral blood mononuclear cells (PBMC) following exposure to a test substance was used to quantitate non-endotoxin pyrogens. See, for example, Dinarello C A, O'Conner J V, LoPreste G: Human leukocyte pyrogen test for detection of pyrogenic material in growth hormone produced by recombinant *Escherichia coli*, *J Clin Microbiol* 1984; 20:323-9; and Poole S, Thorpe R, Meager A, et al: Detection of pyrogen by cytokine release, *Lancet* 1988; 1(8577):130.

Measurement of Peptidoglycans

Peptidoglycan (PG) quantitation was performed with the silkworm larvae plasma (SLP) test (Wako Pure Chemical Industries, Ltd., Osaka, Japan). See, for example, Tsuchiya M, Asahi N, Suzouki F: Detection of peptidoglycan and B-glucan with silkworm larvae plasma test, *FEMS Immunol Medical Micrbiol* 1996; 15:129-34; and U.S. Pat. No. 4,970,152. SLP contains all the factors of the prophenol oxidase (PPO) cascade, a self-defense mechanism of insects. The PPO cascade is initiated by peptidoglycan, in which PPO is ultimately activated to phenol oxidase. The phenol oxidase activity is calorimetrically detected with 3,4-dihydroxyphenylalanine as a substrate. The limit of detection of peptidoglycan in icodextrin solution was found to be 7.4 ng/mL. The SLP test does not detect endotoxins.

As fully disclosed in U.S. Pat. No. 4,970,152, for example, the detection of peptidoglycan (or P-G) can be carried out as follows. A sample containing the peptidoglycan is well mixed with a reagent that includes a fraction which specifically reacts with peptidoglycan ("PG") to prepare a reaction solution. After a certain period of time, an enzymatic activity, e.g., activity of BAEEase, PPAE, PO, etc., in the reaction solution can be measured by a conventional method and compared with calibration curves previously obtained by using PG standard solutions with known concentrations to determine the amount of PG.

Alternatively, it is possible to apply a phenomenon that a time required for the activation of PO depends on the concentration of PG in the sample. That is, after mixing the PG reagent with a sample in the presence of the substrate of PO, a time required for reaching a certain value of the amount of reaction product generated by PO is measured.

By way of example and not limitation, an experimental procedure that utilizes the SLP test can be conducted in accordance with an embodiment of the present invention as follows.

Peptidoglycan (PG) and (1,3)-D-glucan (BG) are components of the cell walls of gram positive bacteria and fungi, respectively. PG and BG are measured with the Silkworm Larvae Plasma (SLP) test. The SLP test contains all the factors of the prophenol oxidase (PPO) cascade, an important self-defense mechanism of insects. The PPO cascade is initiated by peptidoglycan, in which PPO converts 3,4-dihydroxyphenylalanine (DOPA) to melanin. The resulting formation of melanin is calorimetrically detected at 650 nm using a standard plate reader. The raw material icodextrin is tested undiluted and has a limit of detection (LOD) of 0.74 ng/ml (the lowest detectable standard point). The finished product, such as EXTRANEAL, is tested after diluting tenfold in order to mitigate the matrix inhibition caused by the presence of electrolytes. The sample dilution step results in a LOD of 7.4 ng/ml after correcting for the 1:10 dilution.

Animal Studies

No Observed Effect Level (NOEL) for peptidoglycan in icodextrin was determined in a rat model. A total of 45 male Sprague-Dawley rats (Harlan Inc; Indianapolis, Ind., USA), weighing 255-280 g were divided into 9 equal groups. Each group received a single intraperitoneal injection of icodextrin spiked with 0, 1, 5, 10, 50, 100, 500, 1000 or 5000 ng/mL peptidoglycan at a dose of 35 mL/kg. Peptidoglycan derived from *Staphylococcus aureus* (Toxin Technology Inc., Sarasota, Fla., USA) was used in these experiments. Six hours post injection, the rats were sacrificed, and the fluid in the peritoneal cavity was quantitatively collected by determining the weight and volume. Peritoneal fluid was analyzed for nucleated cell counts and differential counts, total protein, and IL-6 and TNF-a concentrations.

Statistical Analysis

Post market surveillance data on several hundred batches of icodextrin manufactured between July 2000 and September 2002 were analyzed to determine an association between peptidoglycan level and the incidence of aseptic peritonitis. To accumulate sufficient complaint frequencies to effectively display complaints per million (CPM), data were classified into peptidoglycan level in a log scale, namely, <7.4, >7.4-15, >15-30, >30-60, and ?60 ng/mL. For each of peptidoglycan concentration range, the total complaints and the total units sold were calculated. The CPM units sold were computed as the total complaints divided by the total units sold multiplied by one million. Negative binomial regression was used to assess the association between CPM and peptidoglycan level. The statistical analysis was performed using the SAS procedure GENMOD (SAS Institute, Cary, N.C., USA).

Clinical Cases

According to reports received through the BAXTER HEALTHCARE CORPORATION's global pharmacovigilance system in 2000, the frequency [(number of complaints=number of patients treated)×100] of aseptic peritonitis was 0.095%. There was a steady increase in reported cases in 2001 to a peak frequency of 1.04% in March 2002. The patients were rarely febrile or toxic in appearance; abdominal pain was modest to absent; the dialysate was cloudy and cellular with dialysate cell counts varying from 300 to 3500/mm$^3$ (variable percentages of neutrophils, lymphocytes, and macrophages without eosinophils). Unlike bacterial peritonitis, there was no change in ultrafiltration or peritoneal permeability for small solutes. Blood and dialysate cultures were invariably negative. Antibiotics were variably instituted by the local physicians. All clinical signs resolved upon stopping icodextrin. In some cases, icodextrin was restarted, and aseptic peritonitis recurred. BAXTER HEALTHCARE CORPORATION initiated a voluntary worldwide recall of several hundred batches of icodextrin in May 2002.

Chemical and Physical Investigations of Icodextrin

Extensive chemical and physical investigations of recalled icodextrin batches were performed. These analyses did not reveal any differences in molecular weight distribution of icodextrin, percent branching of glucosidic bonds, or trace volatile and semi-volatile organic impurities between the batches associated with aseptic peritonitis and those not associated with adverse clinical events. All solution components of complaint batches of icodextrin-containing dialysate were within the product specifications and met current Pharmacopoeia standards.

Dialysate Effluent Analysis

A marked elevation in IL-6 concentration was observed in the dialysate effluent from a patient with aseptic peritonitis compared to control effluent (>5000 versus 59 pg/mL, respectively). An increase in protein concentration was noted with the complaint sample compared to the control (236 mg/dL versus 125 mg/dL, respectively). There was no difference in icodextrin and its metabolites (glucose polymers with degree of polymerization from 2 to 7) between the complaint and control samples. These results indicated that neither icodextrin nor its metabolites were the likely cause of aseptic peritonitis.

Pyrogen Analysis of Icodextrin

Endotoxin levels in all the icodextrin samples associated with aseptic peritonitis were found to be within the product limit (<0.25 EU/mL) as determined by the LAL test. In rabbit pyrogen tests, there was no increase in temperature with either complaint or non-complaint icodextrin batches. However, an increase in IL-6 response in the in vitro PBMC assay was observed with both complaint icodextrin-containing dialysate batches and the icodextrin raw material used to manufacture the complaint batches of peritoneal dialysate as illustrated in Table 1 below:

TABLE 1

IL-6 response of complaint and non-complaint batches of icodextrin in the PBMC assay. In this assay, an IL-6 response of greater than 500 pg/mL is considered a positive pyrogenic response.

| Test Sample | Donor 023 pg/mL | Donor 022 pg/mL | Donor 011 pg/mL |
|---|---|---|---|
| Control Medium[a] | 45 | 24 | 50 |
| Positive Control[b] | 12,000 | 10,000 | 10,000 |
| Negative Control[c] | 130 | 92 | 150 |
| Icodextrin (non-complaint) | 330 | 350 | 110 |
| Icodextrin (complaint) | 5,100 | 7,000 | 970 |
| Icodextrin (complaint) | 4,200 | 4,200 | 700 |
| Icodextrin raw material (complaint) | 9,300 | 780 | 1,600 |
| Icodextrin raw material (non- | 91 | 100 | 130 |

[a]Eagle minimum essential medium with supplemental components,
[b]Baxter experimental product,
[c]Glucose containing standard peritoneal dialysis solution The IL-6 provoking substance in the complaint samples was unaffected in the presence of polymyxin B, thus suggesting that it was not LPS. See, for example, Pool E J, Johaar G, James S, et al: Differentiation between endotoxin and non-endotoxin pyrogens in human albumin solutions using an ex vivo whole blood culture assay, J Immunoassay 1999; 20:79-89. In a filtration experiment using a 30 kD molecular weight cut-off filter, the contaminant producing the inflammatory response in the PBMC assay was found in the retentate, suggesting the molecular weight of the substance was >30 kD, i.e. larger than icodextrin. The negative assays for LPS, but positive PBMC IL-6 response indicated that the likely cause of aseptic peritonitis was a non-endotoxin, pyrogen contaminant in icodextrin raw material used to manufacture the final peritoneal dialysis solution.

Peptidoglycan and Microbiological Analysis

Figure 1:
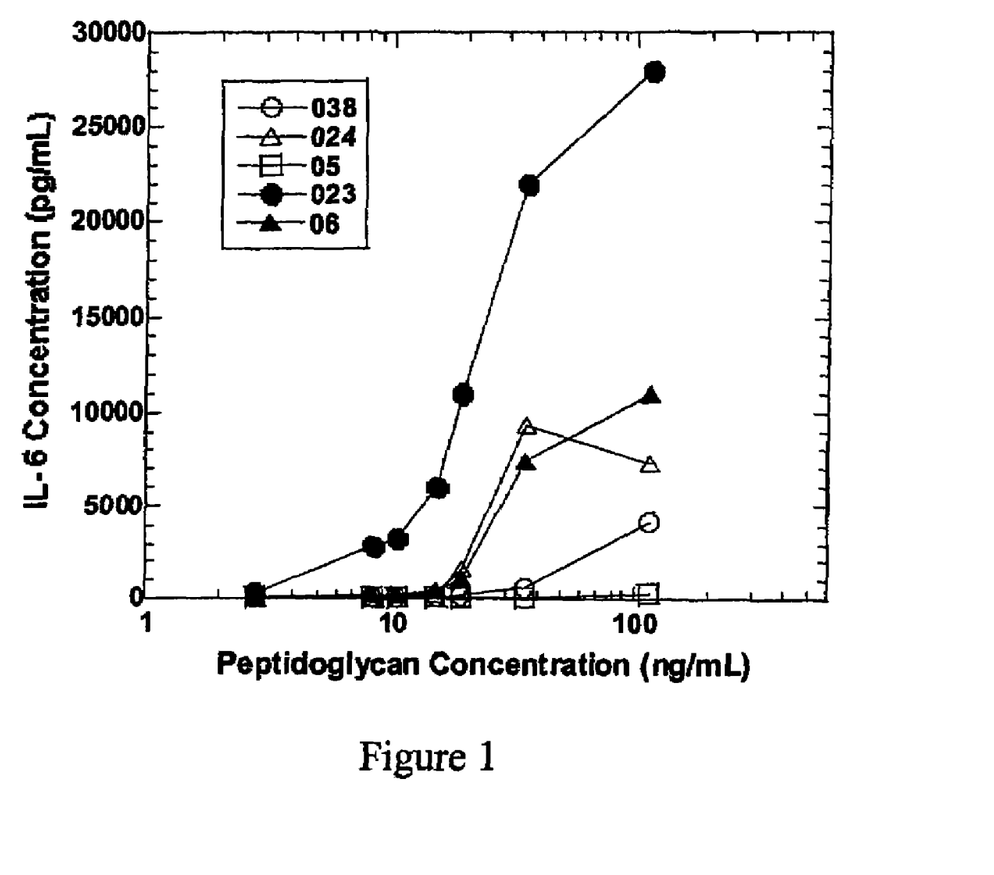
FIG. 1 illustrates a correlation between IL-6 response in a PBMC assay and peptidoglycan concentration in icodextrin. IL-6 response was measured in freshly isolated monocytes from healthy volunteers. Each symbol and line represent data from a single donor.

Analysis of several hundred recalled batches of icodextrin indicated that 41% of the batches were contaminated with peptidoglycan that was detected by the SLP assay. Peptidoglycan concentrations ranged from the detection limit of 7.4 ng/mL to 303 ng/mL. Because the manufacture of icodextrin from maltodextrin requires heat and acidification, a microbiological investigation for the presence of fastidious organisms was undertaken. Early steps of icodextrin were found to be contaminated with a thermophilic, acidiophilic, gram positive organism, *Alicyclobacillus acidocaldarius*. *Alicyclobacillus* was the source of the contaminating peptidoglycan. Heat and sterile filtration procedures applied to the near final product eliminated the bacteria, but not the peptidogycan contaminants. A positive correlation was found between peptidoglycan levels in icodextrin and the IL-6 response observed in the PBMC assay (See, FIG. 1). Substantial variability in the IL-6 response was seen between donors suggesting a range of sensitivities to peptidoglycan.

Animal Studies

Figure 2:
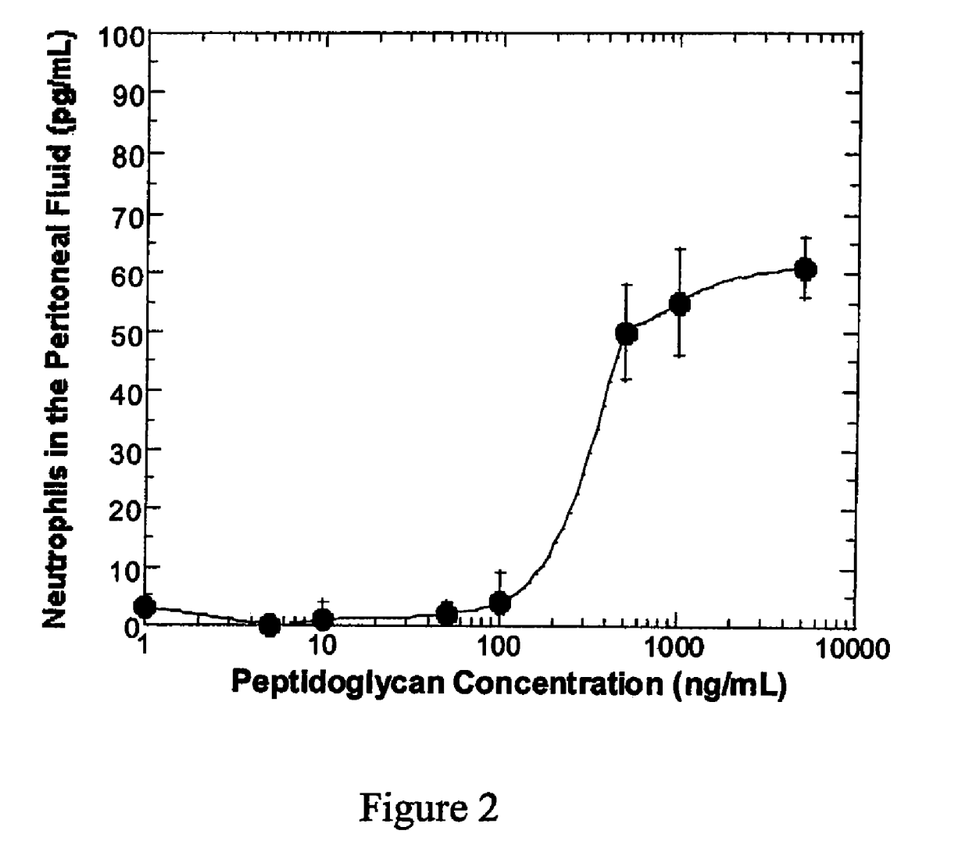
FIG. 2 illustrates an effect of peptidoglycan on the infiltration of neutrophils in the peritoneal fluid of rats. Peritoneal fluid was collected six hours after single injection (35 mLJkg) of icodextrin containing peptidoglycan.
Figure 3:
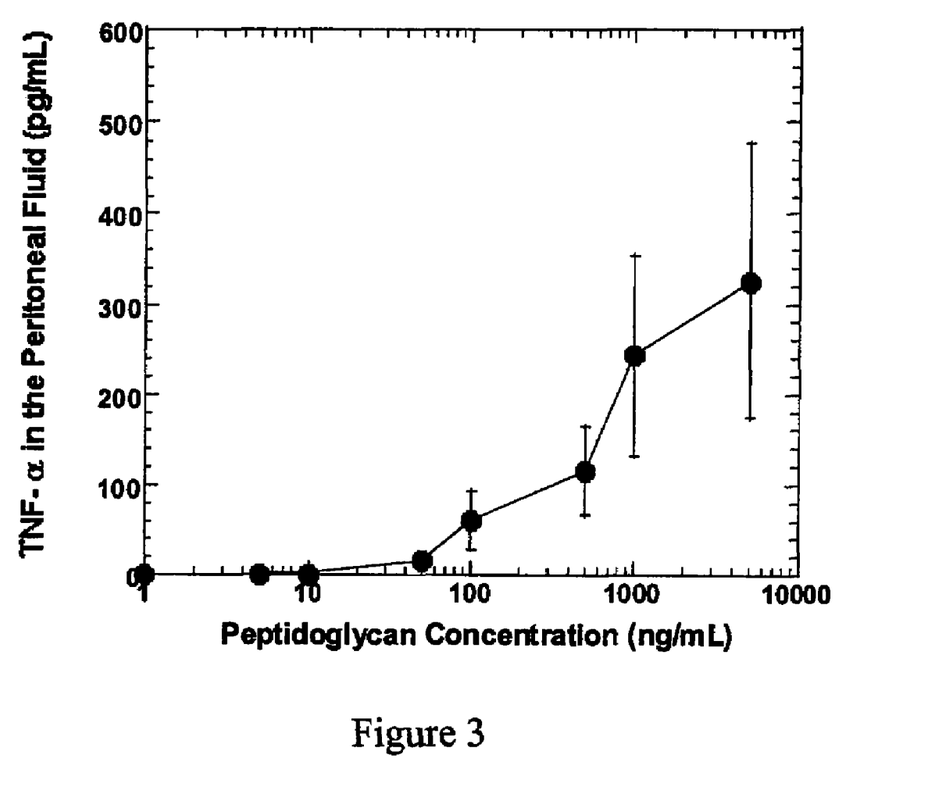
FIG. 3 illustrates an effect of peptidoglycan on TNF-a in the peritoneal fluid of rats.
Figure 4:
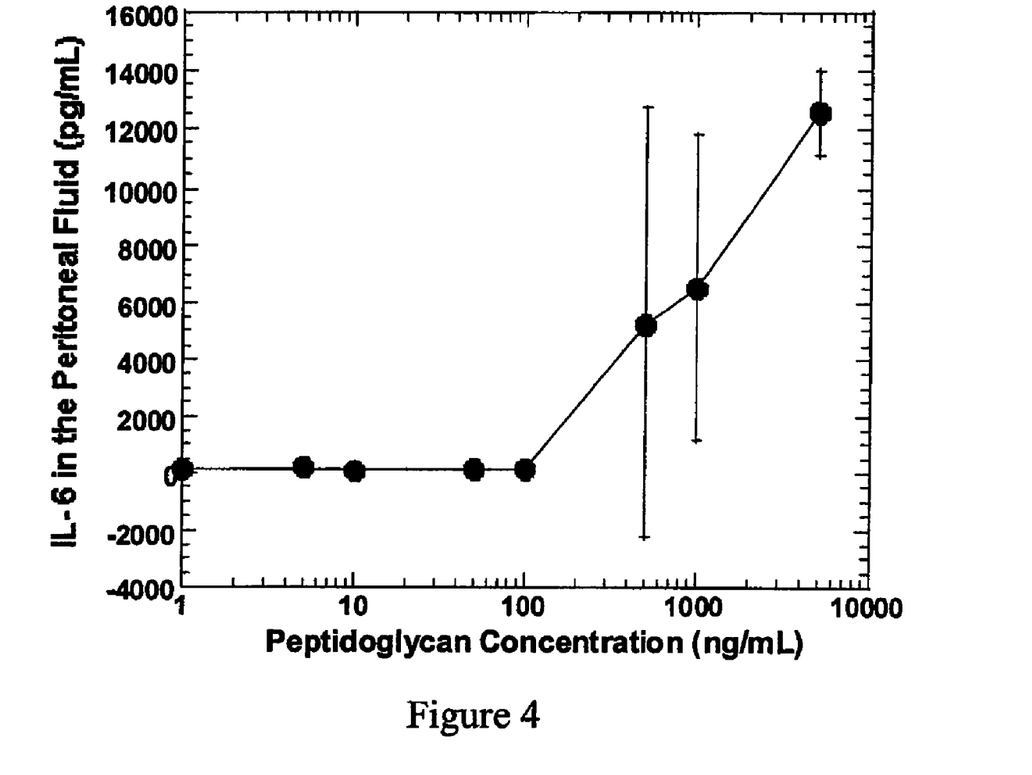
FIG. 4 illustrates an effect of peptidoglycan on IL-6 in the peritoneal fluid of rats.

The effects of intraperitoneal administration of peptidoglycan in rats was investigated in order to establish a NOEL. This can be used to establish a regulatory specification for icodextrin manufacturing. Total protein, white blood cells and neutrophils were elevated in the peritoneal fluid of icodextrin+peptidoglycan-treated rats compared to control rats that received icodextrin without peptidoglycan. Infiltration of neutrophils in peritoneal fluid showed a dose dependent increase with a NOEL at 100 ng/mL (See, FIG. 2). Both inflammatory cytokines showed dose dependent increases with NOEL values at 10 ng/mL for TNF-a (See, FIG. 3) and 100 ng/mL for IL-6 (See, FIG. 4). The lowest NOEL for peptidoglycan was for TNF-a response which was 10 ng/mL. Based on these findings, the inventors effectively determined and established the amount of peptidoglycan that can be present in a peritoneal dialysis solution without causing peritonitis.

Correlation Between Peptidoglycan and Aseptic Peritonitis

A positive correlation was found between peptidoglycan concentration in icodextrin and CPM as illustrated in Table 2 below:

TABLE 2

Correlation between Complaints Per Million (CPM) units sold and peptidoglycan concentration in icodextrin solution

| Peptidoglycan (ng/mL) | Total units sold | Total complaints | CPM per units sold[a] |
|---|---|---|---|
| ≦7.4 | 2906643 | 53 | 18.2 |
| >7.4-15 | 835539 | 10 | 12.0 |
| >15-30 | 349503 | 10 | 28.6 |
| >30-60 | 231330 | 8 | 34.6 |
| ≧60 | 415099 | 105 | 253.0 |

[a]Complaints Per Million (CPM) units sold was computed as the total complaints divided by the total units sold multiplied by one million.

The baseline CPM was 18.2, when peptidoglycan levels were below the detection limit of 7.4 ng/mL. In contrast, the CPM was 252.9, when peptidoglycan levels were equal to or greater than 60 ng/mL. The association between CPM and peptidoglycan was highly significant (p<0.0001).

Incidence of Aseptic Peritonitis Following Corrective Action

In May 2002, BAXTER HEALTHCARE CORPORATION recalled all batches of icodextrin contaminated with peptidoglycan at a concentration >10 ng/mL, as well as all lots that were not assayed for peptidoglycan at the time of the recall. In addition, an internal regulatory specification for peptidoglycan below the detection limit of the assay (<7.4 ng/mL) was implemented for product release. Routine, serial monitoring for peptidoglycan and thermophilic bacteria was implemented. The peptidoglycan concentrations in all the recent batches manufactured have been below the detection limit of the SLP test and are devoid of an IL-6 eliciting agent by the PBMC assay.

Figure 5:
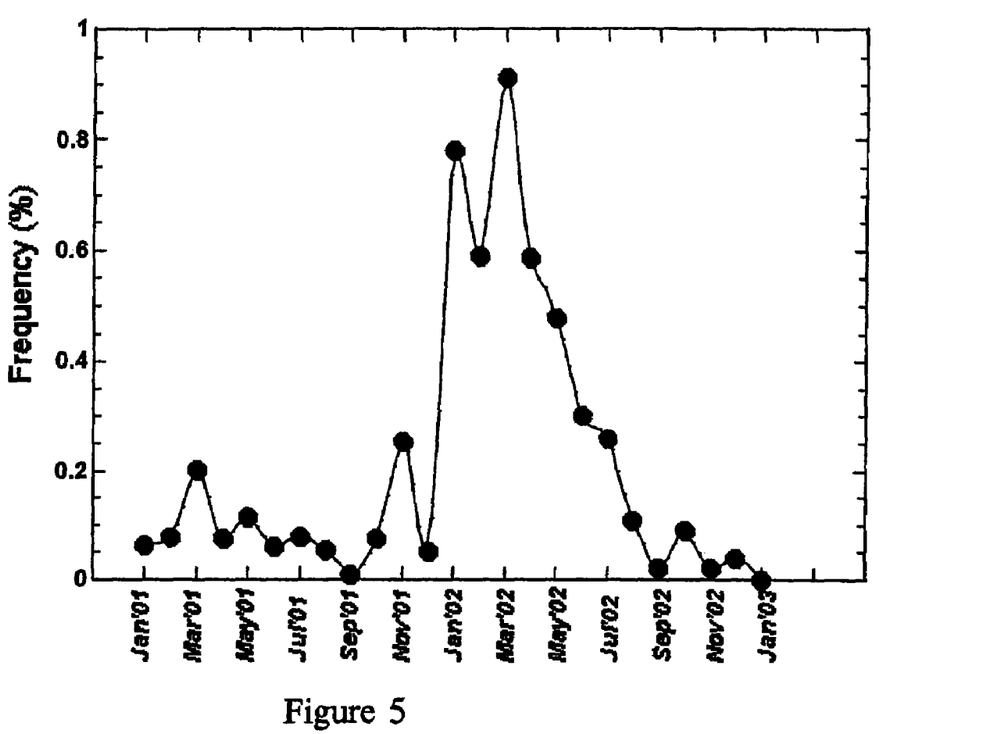
FIG. 5 illustrates frequency (%) of aseptic peritonitis reported with use of icodextrin.

FIG. 5 shows the incidence rate of aseptic peritonitis by month beginning September 2001 to January 2003. The frequency of complaints has decreased from a peak value of 1.04% in March 2002 to 0.013% in January 2003 following the implementation of corrective actions. The number of patients using a commercially-available peritoneal dialysis solution known as EXTRANEAL from BAXTER HEALTHCARE CORPORATION during this period remained at approximately 7,000. These results suggest that corrective actions have been effective in preventing excess complaints of aseptic peritonitis due to peptidoglycan contamination in icodextrin-containing dialysis solution.

As previously discussed, in an embodiment, the present invention relates to methods and compositions that employ the detection of peptidoglycan in peritoneal dialysis solutions. This allows testing for bacterial fragments as peptidoglycans are the major cell wall component of gram positive organisms. In this regard, peptidoglycan detection can be effectively utilized to prevent peritonitis in patients that use the peritoneal dialysis solutions, such as peritoneal dialysis solutions that contain a glucose polymer including icodextrin and the like.

In another embodiment, the present invention includes modified bioburden testing to detect the presence of certain gram positive organisms, such as acidophilic thermophilic organisms. Such organisms were undectable under current Pharmacopoeia standards due to the underlying conditions being used. The inventors determined that such bioburden testing can detect the presence of gram positive bacteria, such as acidophilic thermophilic organisms, when conducted at a pH of about 4.0 to 5.0 and at a temperature of 50 to 60° C. in addition to at a pH of about 7.0 to 7.4 and at a temperature as described in various Pharmacopoeias. This type of testing can be utilized to detect the gram positive organisms in addition to the testing for bacterial fragments through detection of peptidoglycans as previously discussed.

In an embodiment, the present invention provides methods for manufacturing a peritoneal dialysis solution. The method can include any suitable number and type of processing stages. For example, the process includes providing a glucose polymer; adding a reagent to the glucose polymer wherein the reagent is capable of reacting with a peptidoglycan; determining an amount of the peptidoglycan; and using the glucose polymer to make the peritoneal dialysis solution if it is determined that a sufficiently low level of the peptidoglycan is present in the glucose polymer. If the amount of peptidoglycan or the like exceeds this level, such as about 10 ng/mL or less, the glucose polymer can be further processed to remove the peptidoglycan or the like in order to achieve a sufficiently low level of same. The glucose polymer can be further processed in any suitable manner. In an embodiment, the glucose polymer can be processed with any suitable number and type of separation devices, such as an affinity columns with resins that specifically bind peptidoglycan and/or the like.

In an embodiment, the present invention provides compositions, such as glucose polymer compositions that can be used to prepare peritoneal dialysis solutions. A variety of different and type of compositions and solutions containing same can be utilized. For example, the type of compositions and solutions can be found in U.S. Pat. No. 4,761,237, entitled "PERITONEAL DIALYSIS SOLUTION CONTAINING CARBOHYDRATE POLYMERS; U.S. Pat. No. 4,886,789, entitled "PERITONEAL DIALYSIS AND COMPOSITIONS FOR USE THEREIN"; U.S. Pat. No. 6,077,836, entitled "PERITONEAL DIALYSIS AND COMPOSITIONS FOR USE THEREIN"; and U.S. Pat. No. 6,248,726 B1, entitled "METHOD OF PERITONEAL DIALYSIS USING GLUCOSE POLYMER SOLUTIONS, the disclosures of which in their entirety are incorporated herein by reference. Additional examples of compositions and solutions containing same can be found in U.S. patent application Ser. No. 10/327,264, entitled BIOCOMPATIBLE DIALYSIS FLUIDS CONTAINING ICODEXTRINS, filed on Dec. 20, 2002; and U.S. patent application Ser. No. 09/206,063, entitled PERITONEAL DIALYSIS SOLUTION CONTAINING MODIFIED ICODEXTRINS, filed on Dec. 4, 1998, the disclosures of which in their entirety are incorporated herein by reference. In an embodiment, the peritoneal dialysis solutions can include EXTRANEAL by BAXTER HEALTHCARE CORPORATION or suitable modifications thereof.

In an embodiment, the present invention includes methods of providing peritoneal dialysis, such as continuous ambulatory peritoneal dialysis and automated peritoneal dialysis. In continuous ambulatory peritoneal dialysis, the patient performs several drain, fill, and dwell cycles during the day, for example, about four times per day. Each treatment cycle, which includes a drain, fill and dwell, takes about four hours.

Automated peritoneal dialysis is similar to continuous ambulatory peritoneal dialysis in that the dialysis treatment includes a drain, fill, and dwell cycle. However, a dialysis machine automatically performs three or more cycles of peritoneal dialysis treatment, typically overnight while the patient sleeps.

With automated peritoneal dialysis, an automated dialysis machine fluidly connects to an implanted catheter or the like. The automated dialysis machine also fluidly connects to a source or bag of fresh dialysis solution and to a fluid drain. The dialysis machine pumps spent dialysis solution from the peritoneal cavity, through the catheter, to the drain. The dialysis machine then pumps fresh dialysis solution from the source, through the catheter, and into the patient's peritoneal cavity. The automated machine allows the dialysis solution to dwell within the cavity so that the transfer of waste, toxins and excess water from the patient's bloodstream to the dialysis solution can take place. A computer controls the automated dialysis machine so that the dialysis treatment occurs automatically when the patient is connected to the dialysis machine, for example, when the patient sleeps. In this regard, the dialysis system automatically and sequentially pumps fluid into the peritoneal cavity, allows for dwell, pumps fluid out of the peritoneal cavity, and repeats the procedure.

Several drain, fill, and dwell cycles will occur during the treatment. Also, a final volume "last fill" is typically used at the end of the automated dialysis treatment, which remains in the peritoneal cavity of the patient when the patient disconnects from the dialysis machine for the day. Automated peritoneal dialysis frees the patient from having to manually perform the drain, dwell, and fill steps during the day. In an embodiment, automated peritoneal dialysis can be performed by utilizing an admix device, such as ADMIX HOMECHOICE by BAXTER HEALTHCARE CORPORATION or suitable modifications thereof.

In an embodiment, the present invention provides a test to determine if a peritoneal dialysis solution, such as an icodextrin-based solution, includes gram positive microbial contaminants that exceeds a level sufficient to cause peritonitis in the patient that uses same. To this end, the present invention employs a detection protocol that detects the presence of peptidoglycan. The protocol utilizes a reagent, such a reagent derived from a silkworm larvae plasma, for such purpose. Modified bioburden testing can also be utilized as previously discussed. It should be appreciated that the detection procedure can be carried out at any suitable stage prior to use of the peritoneal dialysis solution.

For example, the reagent can be added to a glucose polymer composition, such as an icodextrin composition, in raw material form to determine the presence of peptidoglycan. If the level of peptidoglycan is at a sufficiently low level, the composition can then be utilized to prepare the peritoneal dialysis solution. Modified bioburden testing can also be utilized to determine the presence of gram positive microbial contaminants in raw materials that can be used to make the peritoneal dialysis solutions, such as glucose polymers, according to an embodiment and as further discussed above.

In another embodiment, the reagent can be added to the peritoneal dialysis solution, such as after the sterilization process in finished product form. For example, the reagent can be added to the peritoneal dialysis solution that is contained within any suitable solution bag, such as a single-chambered solution bag or a multi-chamber solution bag. An example of a multi-chamber solution bag or container is provided in U.S. Pat. No. 5,431,496, the disclosure of which in its entirety is incorporated herein by reference.

As described herein, all patent applications and publications including patent publications are incorporated herein by reference in their entirety.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A method of providing dialysis to a patient, the method comprising:
   preparing a dialysis solution including:
   a) providing a glucose polymer in a powder form;
   b) performing a modified bioburden test on the glucose polymer to detect contaminating *Alcyclobacillus acidocaldarius;*
   c) preparing a glucose polymer solution using the powder form of the glucose polymer;
   d) sterilizing the glucose polymer solution;
   e) adding a reagent derived from silkworm larvae plasma to the sterilized glucose polymer solution, wherein the reagent is reactive with peptidoglycan to determine a peptidoglycan concentration; and
   f) using the sterilized glucose polymer solution to prepare the dialysis solution if the peptidoglycan concentration is determined to be about 10 ng/mL or less; and
   providing the dialysis solution to the patient.

2. The method of claim 1, wherein the dialysis solution is a peritoneal dialysis solution.

3. The method of claim 2, wherein the peritoneal dialysis solution is provided during peritoneal dialysis selected from the group consisting of an automated peritoneal dialysis and a continuous peritoneal dialysis.

4. The method of claim 1, wherein the reaction with the reagent initiates a serine protease cascade.

5. The method of claim 4, wherein the serine protease cascade includes a prophenol oxidase cascade.

6. The method of claim 1, wherein the peptidoglycan concentration is determined by a calorimetric measurement.

7. The method of claim 1, wherein the modified bioburden test includes testing for the *Alicyclobacillus acidocaldarius* at a pH of less than about 5.0.

8. The method of claim 1, wherein the modified bioburden test includes testing for the *Alicyclobacillus acidocaldarius* at a temperature of 50° C. to 60° C.

9. The method of claim 1, wherein the glucose polymer includes icodextrin.

* * * * *